(12) United States Patent  
Segat et al.

(10) Patent No.: US 8,808,866 B2  
(45) Date of Patent: *Aug. 19, 2014

(54) COATED ELASTOMERIC ARTICLE AND METHOD FOR MAKING A COATED ELASTOMERIC ARTICLE

(71) Applicants: Precision Components, Inc., Rosemount, MN (US); Xela Corporation, Rosemount, MN (US)

(72) Inventors: Anil Segat, Mendota Heights, MN (US); Andreas Brown, Prior Lake, MN (US)

(73) Assignees: Precision Components, Inc., Rosemount, MN (US); Xela Corporation, Rosemount, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/760,036

(22) Filed: Feb. 5, 2013

(65) Prior Publication Data

US 2013/0149354 A1  Jun. 13, 2013

Related U.S. Application Data

(63) Continuation of application No. 13/758,697, filed on Feb. 4, 2013, which is a continuation of application No. 11/985,252, filed on Nov. 14, 2007, now Pat. No. 8,365,314.

(60) Provisional application No. 60/858,854, filed on Nov. 14, 2006.

(51) Int. Cl.
 *B32B 25/04* (2006.01)
 *A41D 19/015* (2006.01)

(52) U.S. Cl.
 USPC ............. 428/451; 2/106; 427/2.3; 427/427.7; 427/430.1; 428/34.7; 428/35.7; 428/36.8; 428/447; 428/474.4; 428/492; 428/522; 523/106; 524/21; 524/106

(58) Field of Classification Search
 USPC ....... 523/106; 524/21, 106; 2/161.7; 427/2.3, 427/427.7, 430.1; 428/34.7, 35.7, 36.8, 428/447, 451, 474.4, 492, 522

See application file for complete search history.

(56) References Cited

U.S. PATENT DOCUMENTS

| | | | |
|---|---|---|---|
| 6,274,154 | B1 | 8/2001 | Chou |
| 6,423,328 | B2 | 7/2002 | Chou |
| 6,630,152 | B2 | 10/2003 | Chou |
| 2004/0122382 | A1 | 6/2004 | Johnson et al. |
| 2005/0127552 | A1 | 6/2005 | Modha et al. |
| 2005/0228538 | A1 | 10/2005 | Limburger |
| 2006/0115653 | A1 | 6/2006 | Soerens et al. |

FOREIGN PATENT DOCUMENTS

| | | |
|---|---|---|
| DE | 41 36 540 | 5/1992 |
| DE | 101 14 060 | 1/2002 |
| EP | 1 709 879 | 10/2006 |
| WO | WO 2005/072856 | 8/2005 |

OTHER PUBLICATIONS

PCT/US07/23884 International Search report dated Mar. 31, 2008, 2 pages.
PCT/US07/23884 Supplemental European Search report dated Feb. 25, 2010, 5 pages.

*Primary Examiner* — D. S. Nakarani
(74) *Attorney, Agent, or Firm* — Fulbright & Jaworski LLP; Scott D. Rothenberger

(57) ABSTRACT

An elastomeric article, such as a glove or a condom, is coated with a compound containing silicone, collagen and allantoin.

3 Claims, 4 Drawing Sheets

US 8,808,866 B2

COATED ELASTOMERIC ARTICLE AND METHOD FOR MAKING A COATED ELASTOMERIC ARTICLE

CROSS REFERENCE TO RELATED APPLICATION

This application is a continuation application of U.S. patent application Ser. No. 13/758,697, filed Feb. 4, 2013, which is a continuation of U.S. patent application Ser. No. 11/985,252, filed Nov. 14, 2007, now U.S. Pat. No. 8,365,314 B2 which claims the benefit of U.S. Provisional Patent Application No. 60/858,854, filed Nov. 14, 2006, the disclosure of which are incorporated by reference herein.

FIELD OF THE INVENTION

The present invention relates generally to a protective elastomeric article, and more particularly to a protective elastomeric article, such as a glove, for medical and non-medical uses that is coated for beneficial effect.

BACKGROUND OF THE INVENTION

Disposable gloves made from various synthetic and natural raw materials are used to protect against transmission of viral and bacterial agents and other pathogens, and to protect against chemical and radiological contamination. Users who must wear gloves for extended periods often suffer from dried or chapped hands, skin irritation, hand fatigue and premature wrinkling.

Gloves using aloe vera as a moisturizer are described in U.S. Pat. Nos. 6,274,154, 6,423,328, 6,630,152. Aloe vera is used in many skin care products, but it has an oil content that can have an adverse reaction when used with natural rubber and other materials, breaking down capability of rubber to act as a barrier. Some gloves also use lotions, which may have a similar effect on the barrier properties of gloves made from different raw materials. Other coatings used in gloves include cucumber extract and/or glycerin, but there is no evidence that common moisturizers used singly or in combination with another, have significantly improved the therapeutic properties of a disposable glove.

Water soluble silicone has been used as a coating in disposable gloves since 1991, as a moisturizer and lubricant for ease of donning. Silicone has been shown to substantially reduce skin irritations when used in conjunction with natural rubber latex gloves.

Allantoin, a botanical extract of comfrey also known as glyoxyldiureide has been recognized by the US FDA OTC panel as a skin protectant. It is believed to regenerate and stimulate cells, softens skin and acts to remove unhealthy tissue and is an anti-irritant.

Hydrolyzed collagen imparts protective colloid effect to formulations with anti-irritancy benefits. It increases the ability of skin to hold moisture. It is one of the long, fibrous structural proteins whose functions are quite different from those of globular proteins such as enzymes. Strong, tough bundles of collagen called collagen fibers are a major component of the extracellular matrix that supports most tissues and gives cells structure from the outside, but collagen is also found inside certain cells. Collagen has high tensile strength, and is the main component of cartilage, ligaments, tendons, bone and teeth. Along with soft keratin, it is responsible for skin strength and elasticity, and its degradation leads to wrinkles that accompany aging. It strengthens blood vessels and plays a role in tissue development.

SUMMARY OF THE INVENTION

The glove of the present invention incorporates a compound made up of a combination of silicone, allantoin, and collagen. The invention further provides a method of coating a glove with such a compound.

BRIEF DESCRIPTION OF THE DRAWINGS

An exemplary version of an elastomeric article is shown in the figures wherein like reference numerals refer to equivalent structure throughout, and wherein.

DETAILED DESCRIPTION OF PREFERRED EMBODIMENT(S)

Figure 1:
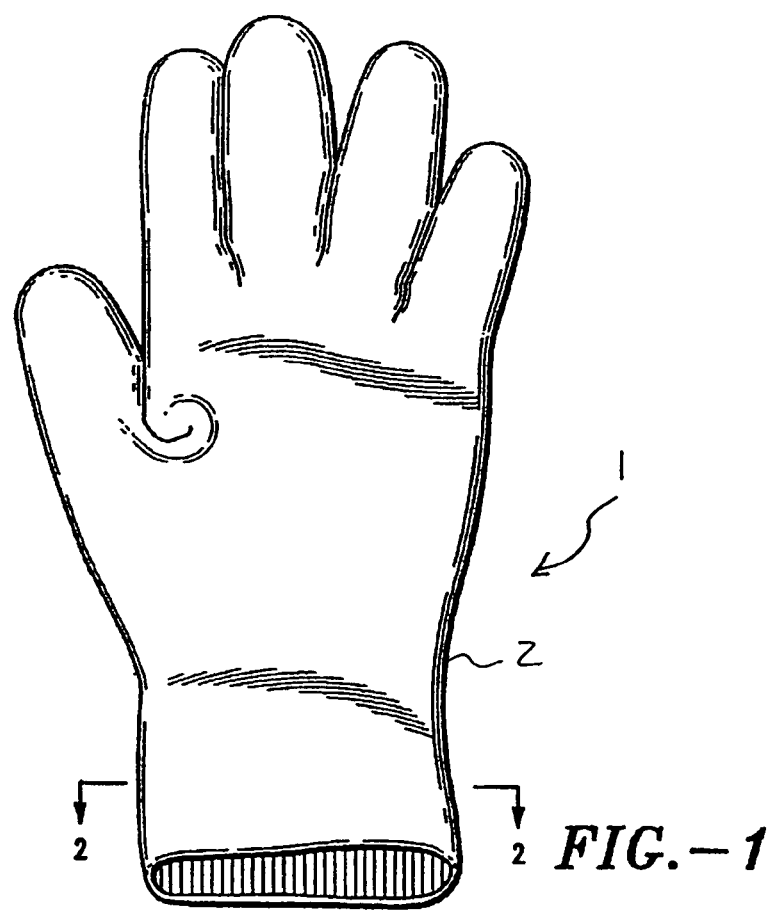
FIG. 1 is a perspective view of an elastomeric article, specifically a glove, according to the present invention.
Figure 2:
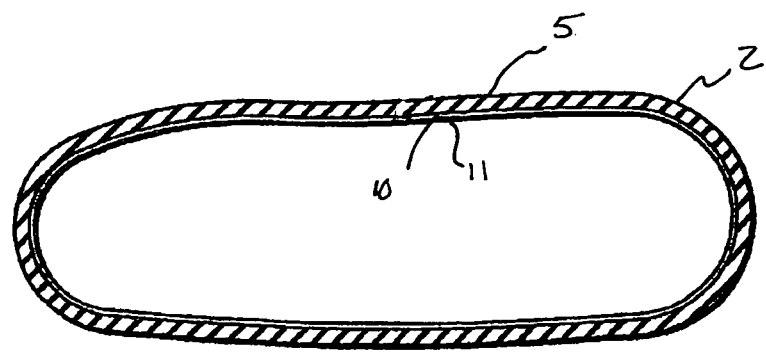
FIG. 2 is a cross section of the elastomeric article of FIG. 1, shown as it is oriented when it is worn during use.

As shown in FIG. 1, an elastomeric article 1 is coated to achieve therapeutic benefits for a user's skin adjacent to the article and to achieve other benefits such as easy donning of the glove. Gloves 2 and condoms (not pictured) are examples of elastomeric articles that may benefit from the coating described herein. As shown in FIG. 2, the glove 2 is formed of an elastomeric substrate 5, made from one of the following materials: natural rubber latex; poly-vinyl choride; synthetic rubber, such as acrylonitrile, chloroprene or neoprene; nylons or any other material or combination of such materials. The substrate 5 has a surface 10 that contacts the skin during use and this surface 10 bears a coating 11 that is of a compound of silicone, allantoin and collagen. The glove substrate 5 in cooperation with the coating 11 prevents moisture from permeating the glove, thereby maintaining the skin's moisture within the glove during use. This retained moisture reacts with the coating 11, yielding a soothing and comfortable therapeutic effect on the skin.

Figure 3:
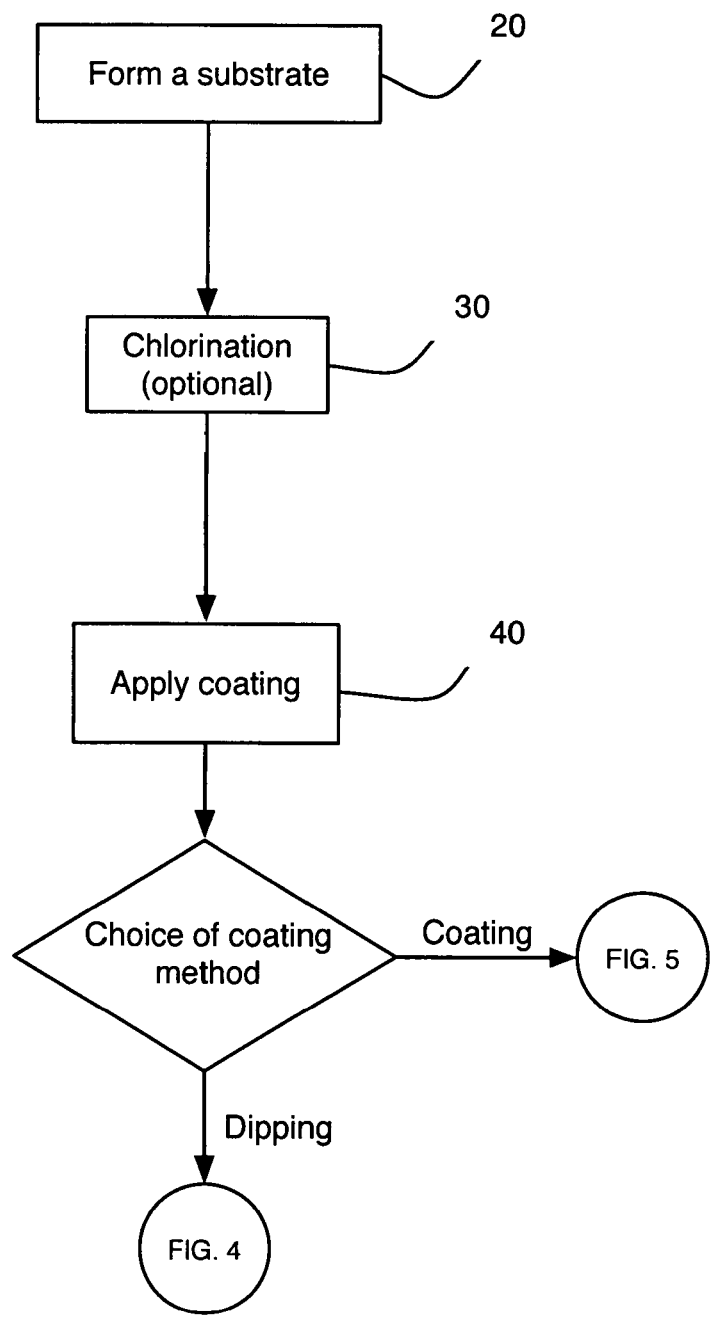
FIG. 3 a flow chart illustrating a portion of the process of making the elastomeric article of FIG. 1.

FIG. 3 illustrates a method of making the elastomeric article 1 of FIGS. 1 and 2. A formed substrate is made (20). The typical process for forming the substrate involves dipping a form, or a plurality of forms, in a pool of raw material. The raw-material-covered form is then dried, the substrate taking the shape of the form. Optionally, a second dip in raw material, followed by drying, may follow to obtain a substrate of the desired thickness. The substrate is then dipped into a pool of leaching material to remove excessive chemical impurities and latex proteins if the substrate is of natural rubber. Optionally, the cuff of the elastomeric article may be beaded according to conventional techniques, such as using rollers or brushes. The substrate is then cured.

Next, the formed substrate, still on the form, will be subjected to optional chlorination (30) to remove impurities and residual proteins that may have come to the surface of the gloves during curing. Optional chlorination (30) is followed by further leaching. As an alternative to or in addition to chlorination (30), the substrate may instead be dipped into a polymer solution that will act as a donning agent to make the surface of the article slippery for easy donning. The thickness of the polymer layer is adjusted by varying the rate at which the form is dipped into the polymer, by varying the speed of the production line, or by adjusting the consistency and density of the polymer, or a combination of these approaches.

Figure 4:
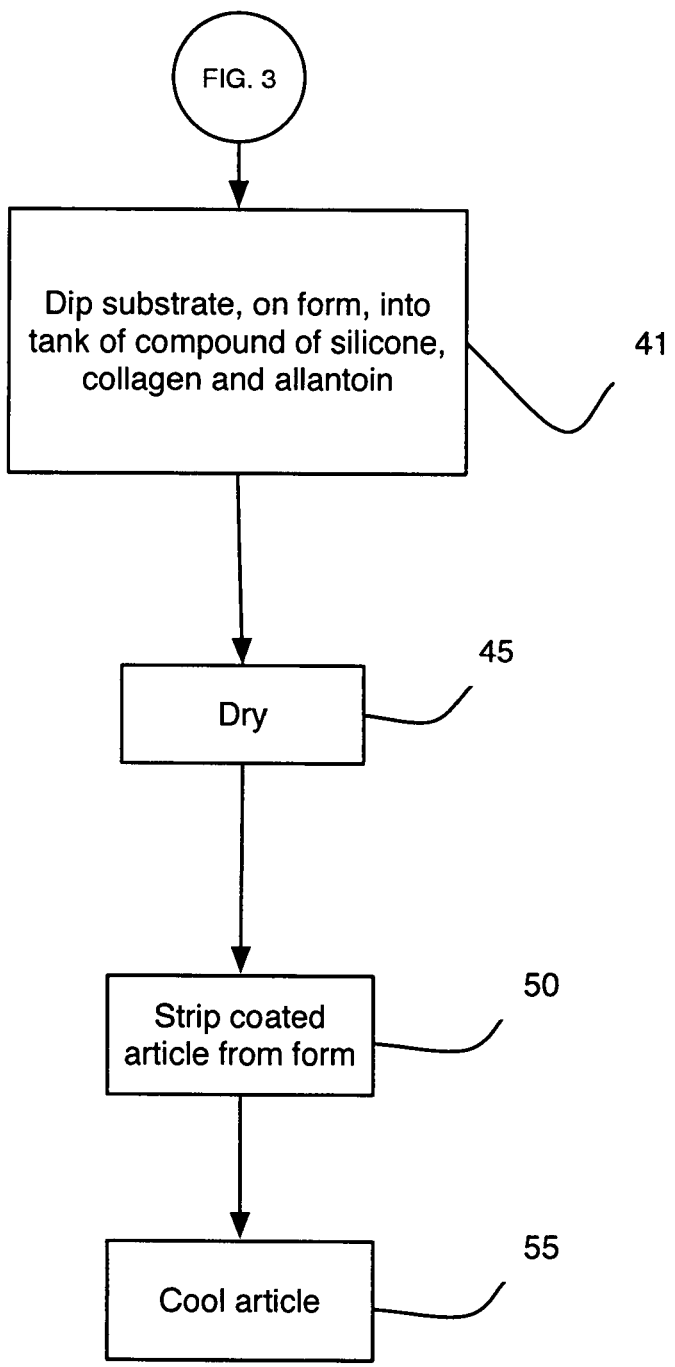
FIG. 4 is a flow chart illustrating one method of applying a coating to a substrate to form the article of FIG. 1.
Figure 5:
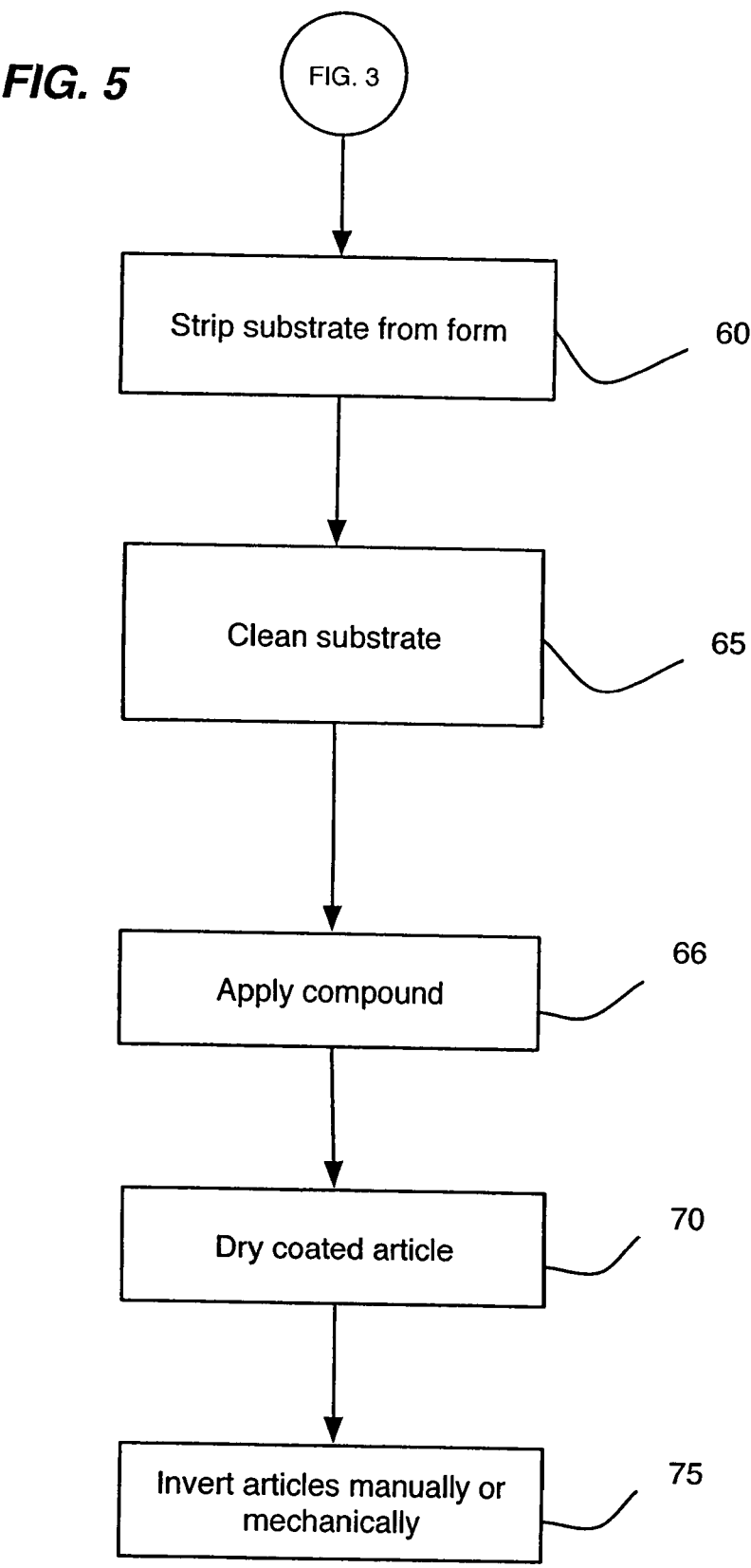
FIG. 5 is a flow chart illustrating an alternative method of applying a coating to a substrate to form the article of FIG. 1.

In step 40, the coating 11 is applied. There are two viable methods for applying the coating 11: a dipping method (FIG. 4) and a spraying method (FIG. 5). To apply the coating 11 by the dipping method, the substrate, still on the form, is dipped (41) into a tank or a series of tanks containing a compound of silicone, collagen and allantoin (hereafter "compound"), described further below.

The following table shows an example of the concentrations, experimentally determined, of the components of the compound and parameters for application by dipping:

| Substance | Concentration (between about) | Temperature (between about) | Time (about) |
|---|---|---|---|
| Silicone polymer solution | 0.1%-2.0% | 30-40 C. ° | 3-8 seconds |
| Collagen | 0.1%-2.0% | 30-40 C. ° | 3-8 seconds |
| Allantoin | 0.1%-2.0% | 30-40 C. ° | 3-8 seconds |

One such embodiment employs water-based silicone polymer solution, hydrolyzed collagen and allantoin powder.

The thickness of the coating 11 is adjusted by varying the rate at which the form is dipped into the compound, by varying the speed of the chain on which the form are mounted, or by adjusting the consistency and density of the compound, or a combination of these approaches.

Through experimentation, the concentrations and parameters shown in the table above were determined to yield a glove of suitable thickness with a noticeable beneficial effect. Higher dipping time yielded a thicker film coating and therefore a thicker glove providing undesired reduction of tactile sense through the glove. Lower dipping time yielded a coating that was too thin to provide a noticeable therapeutic effect. The concentration levels noted in the chart were subjected to and passed biocompatibility tests, determining that these concentrations would not cause allergy problems in users. Higher concentrations yielded uneven coating and drip marks. Lower concentrations did not yield a noticeable therapeutic effect. Higher temperatures cause the compound to be too thin to form the desired layer. At lower temperatures, the components may not dissolve thoroughly or consistently through the compound. Further, at lower temperatures, the coating is not picked up by the substrate in an even manner.

Next, the coated substrate is dried (45), such as by passing the form through a blow drying oven heated to 65-70° C. for about 10 minutes. The heat from the ovens allows the slicone, collagen and allantoin compound gel to evaporate and form an even layer on the surface of the glove.

The coated substrates are then stripped (50) from the forms, turning them inside out, such that the coating 11 resides on the inside surface of the glove 2. The gloves then cool (55).

In the spraying method, FIG. 5, the formed substrate is stripped (60) from the form. Batches of formed substrates are tumbled (65) in a tumbler to which clean water at roughly room temperature is added. The articles are tumbled for about 10 minutes, after which the water is pumped out of the tumbler. The compound, having the same components and concentrations as described above in regard to the dipping method, is then introduced (66) into the tumbler, such as by a spray nozzle while the tumbler continues to tumble the articles. The compound may be introduced one component at a time, or all at once. The tumbling time and the spraying quantity is determined by the tumbler and the spraying mechanism, and is selected to achieve a desired thickness, preferably between 0.02 and 0.04 mm of coating on the substrate. The coated articles are then dried (70) in a dryer and tumbled dry for between 2-3 hours at 45-50° C. After drying, the formed and coated articles are inverted (75) manually or mechanically so that the coated side is on the inside of the article.

In typical manufacturing, to achieve efficiency, the manufacturing process is performed on an assembly line with multiple forms being dipped or dried at one time. The chlorination process and the process of adding a donning agent may optionally be conducted "off-line", using tumblers and dryers.

Although an illustrative version of the article and method of making it is shown, it should be clear that many modifications to the device may be made without departing from the scope of the invention. The above details are provided merely to illustrate a typical process of manifesting the invention into a product. The parameters and process described are a guideline, and may be modified to suit the production environment as long as the end product is within the scope and spirit of this invention. The exact parameters used depend upon a number of variables, such as the raw material used, age of the production line, ultimate user application of the glove, and other factors.

We claim

1. A coated elastomeric substrate, comprising:
   a first coating material comprising silicone;
   a second coating material comprising collagen; and
   a third coating material comprising allantoin, wherein the first, second and third coating materials provide a coating on the elastomeric substrate comprising silicone, collagen and allantoin.

2. The coated elastomeric substrate according to claim 1, wherein the first, second and third coating materials can be provided in any sequence.

3. The coated elastomeric substrate according to claim 1, wherein the silicone is an aqueous based silicone material.

* * * * *